United States Patent
Chang

(10) Patent No.: US 8,641,636 B2
(45) Date of Patent: Feb. 4, 2014

(54) ELECTRONIC VITAL-SIGN MONITORING SYSTEM

(76) Inventor: Kuo-Yuan Chang, New Taipei (TW)

( * ) Notice: Subject to any disclaimer, the term of this patent is extended or adjusted under 35 U.S.C. 154(b) by 0 days.

(21) Appl. No.: 13/592,915

(22) Filed: Aug. 23, 2012

(65) Prior Publication Data

US 2013/0053712 A1 Feb. 28, 2013

(30) Foreign Application Priority Data

Aug. 24, 2011 (TW) .............................. 100130308 A

(51) Int. Cl.
*A61B 5/02* (2006.01)

(52) U.S. Cl.
USPC .......................................................... 600/508

(58) Field of Classification Search
USPC ................. 600/508, 518, 529, 300, 485, 324; 607/44; 705/2
See application file for complete search history.

(56) References Cited

U.S. PATENT DOCUMENTS

| | | | |
|---|---|---|---|
| 6,050,951 A * | 4/2000 | Friedman et al. ............. | 600/485 |
| 7,135,000 B2 | 11/2006 | Chang | |
| 2005/0027207 A1* | 2/2005 | Westbrook et al. ........... | 600/529 |
| 2008/0009917 A1* | 1/2008 | Rossing et al. ................. | 607/44 |
| 2008/0139894 A1* | 6/2008 | Szydlo-Moore et al. ..... | 600/300 |
| 2010/0010360 A1* | 1/2010 | Kurzweil et al. ............. | 600/518 |
| 2010/0057490 A1* | 3/2010 | Kocis et al. ....................... | 705/2 |
| 2010/0317979 A1* | 12/2010 | Kelly ............................ | 600/508 |
| 2012/0136226 A1* | 5/2012 | Wilke ........................... | 600/324 |

\* cited by examiner

*Primary Examiner* — Robert N Wieland
(74) *Attorney, Agent, or Firm* — Muncy, Geissler, Olds & Lowe, PLLC

(57) ABSTRACT

A electronic vital-sign monitoring system is provided here, which uses an external electronic device to compute a physiological value detected by an electronic vital-sign monitoring device and obtain a heart frequency spectrum; and provide power to the electronic vital-sign monitoring system; and further transfer the computed physiological value and the heart frequency spectrum to a database for data integration and incident reporting. In addition to the original function of detecting physiological values, the electronic vital-sign monitoring system further can detect heart frequency spectrum and offers telecare service to help patients, elders and general users according to different requirements.

11 Claims, 2 Drawing Sheets

ELECTRONIC VITAL-SIGN MONITORING SYSTEM

BACKGROUND OF THE INVENTION

1. Field of the Invention

The present invention relates to an electronic vital-sign monitoring system, and more particularly to a multifunctional vital-sign monitoring system with a database such as blood pressure & heart frequency spectrum monitor, blood oxygen & heart frequency spectrum monitor, electrocardiogram & heart frequency spectrum monitor or patient monitor for monitoring heart frequency spectrum.

2. Description of the Prior Art

In recent years, population ageing and low birth rate have gradually become a trend. Therefore, designing and implementing for the elder community (retirement community) is a significant target for community development. Regarding to health care in the community for elders, not only portable electronic are necessary to detect physiological values such as blood pressure, heart rate etc., but a more completed telecare system is required to monitor users' health status. By using medical instruments of telecare system, nursing staff or family members can monitor physiological values such as heart rate, blood pressure or heart frequency spectrum for elders, which enables long-distance caregivers to track and record health status for elders.

By measuring heart rate signals, results can be obtained and then be transformed to frequency spectrum diagram. Transformation for frequency domain uses fast Fourier transform (FFT) algorithm. Generally, the frequency spectrum diagram has 3 to 5 main frequency waveforms. The first main frequency waveform corresponds to heart rate frequency. If there are several disorder frequency waveforms beside the main frequency waveforms, it means the heart rate status appears irregular and can be considered abnormal. Thus, heart rate frequency spectrum can be used to determine heart status.

Because general electronic vital-sign monitoring devices are portable and easy to operate, they are very popular over hospitals, clinics and nursing centers. However, the function of monitoring heart rate frequency spectrum is not included. For elders or patients who need special health care in the community, general electronic vital-sign monitoring devices cannot regularly monitor their heart status.

Since general electronic vital-sign devices cannot detect heart frequency spectrum, users who desire to know heart status must go to major hospitals or medical center for precise examination and physician diagnose, which is very inconvenient especially for patients with mobility problems. If general electronic vital-sign monitoring devices, which are able to detect measuring blood pressure, blood oxygen, heart rate and electrocardiogram etc. used in hospital or clinics or telecare center, can also obtain information of heart frequency spectrum, heart status can be monitored in real-time and it will be very practicable and convenient to patients, elders and general users.

Accordingly, it is highly desirable to develop an electronic vital-sign monitoring system to help patients, elders and general users to monitor their physiological values and heart status immediately.

SUMMARY OF THE INVENTION

The present invention relates to an electronic vital-sign monitoring system which not only has original detection functions but also can detect heart frequency spectrum and offers telecare service. For patients, elders and general users, it can provide proper assistance according to different requirements.

In order to achieve objectives aforementioned, according to one embodiment of the present invention, an electronic vital-sign monitoring system comprises a database; a detection unit, for detecting a physiological value; a processing unit, connected to the detection unit, for computing the physiological value and obtaining a heart frequency spectrum; and a transfer unit, electrically connected to the processing unit, for transferring the physiological value and the heart frequency spectrum to the database, wherein the database is a cloud database or a local database.

According to another embodiment of the present invention, an electronic vital-sign monitoring device is electrically connected to an external electronic device to compose an electronic vital-sign monitoring system further comprising a database, wherein the electronic vital-sign monitoring device comprises a detection unit, for detecting an analogous signal of a physiological value; a conversion unit, connected to the detection unit, for converting the analogous signal to a digital signal of the physiological value; and a connection unit, electrically connected to the conversion unit and the external electronic device. The external electronic device computes the digital signal and obtains a heart frequency spectrum.

The objective, technologies, features and advantages of the present invention will become more apparent from the following description in conjunction with the accompanying drawings, wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed description, when taken in conjunction with the accompanying drawings, wherein.

DESCRIPTION OF THE PREFERRED EMBODIMENT

The detailed description is provided below and the preferred embodiments described are only for the purpose of description rather than for limiting the present invention.

Figure 1:
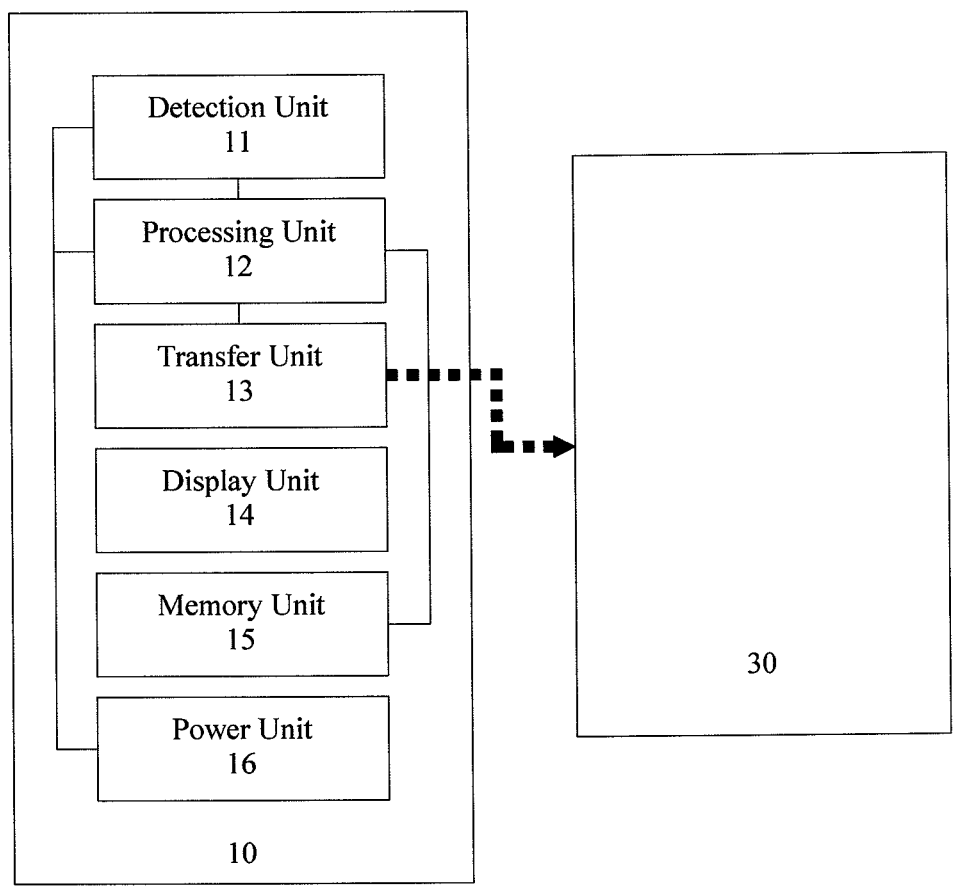
FIG. 1 is a block diagram schematically illustrating the structure of the electronic vital-sign monitoring system according to one embodiment of the present invention.

FIG. 1 is a block diagram schematically illustrating the structure of the electronic vital-sign monitoring system according to one embodiment of the present invention. As shown in the figure, an electronic vital-sign monitoring system 10 comprises a database; a detection unit 11, for detecting a physiological value; a processing unit 12, connected to the detection unit 11, for computing the physiological value and obtaining a heart frequency spectrum; and a transfer unit 13, electrically connected to the processing unit 12, for transferring the physiological value and the heart frequency spectrum to the database 30.

Continue the above description, as shown in FIG. 1, the electronic vital-sign monitoring system 10 further comprises a display unit 14, a memory unit 15 and a power unit 16, wherein the display unit 14 is connected to the processing unit 12 for displaying the physiological value and the heart frequency spectrum; the memory unit 15 is connected to the processing unit 12 for storing the physiological value and the heart frequency spectrum; the power unit 16 is connected to the processing unit 12 and the detection unit 11 for providing power.

In one embodiment, the detection unit 11 is an electronic blood pressure monitor for detecting physiological information such as blood pressure. The database 20 can be a cloud database or a local database. After receiving the physiological value or heart frequency spectrum, the database will then integrate and archive the data to enable the subjects, their family members or nursing staff to view the results on the internet. Once the physiological value or heart frequency spectrum appears abnormal or exceed threshold value, reporting mechanism will be activated to inform the subjects, their family members and nursing staff. On the other hand, the electronic vital-sign monitoring system can be a single functional system for detecting physiological values or a multi-functional patient monitoring system.

Figure 2:
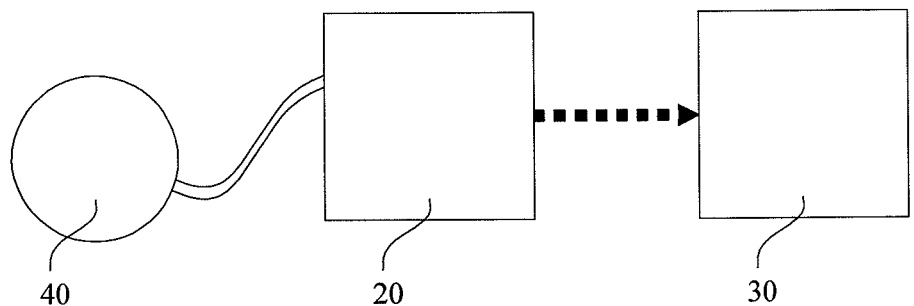
FIG. 2 is a schematic diagram illustrating the configuration of the electronic vital-sign monitoring system according to another embodiment of the present invention.
Figure 3:
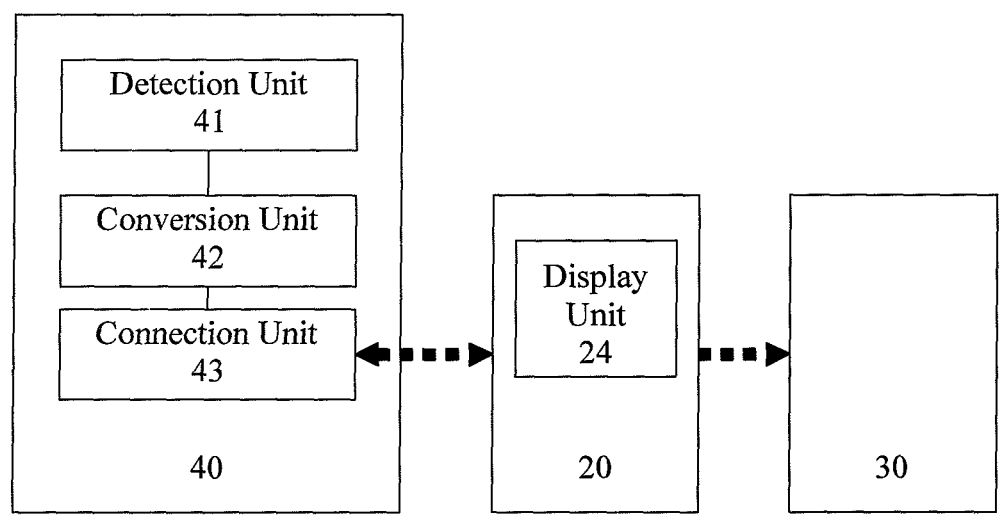
FIG. 3 is a block diagram schematically illustrating the structure of the electronic vital-sign monitoring system according to FIG. 2.

FIG. 2 is a schematic diagram illustrating the configuration of the electronic vital-sign monitoring system according to another embodiment of the present invention. As shown in the figure, an electronic vital-sign monitoring system 10 comprises an electronic vital-sign monitoring device 40, an external electronic device 20 and a database 30, wherein the electronic vital-sign device 40 is electrically connected to the external electronic device 20. FIG. 3 is a block diagram schematically illustrating the structure of the electronic vital-sign monitoring system according to FIG. 2. As shown in the figure, the electronic vital-sign monitoring device 40 comprises a detection unit 41, for detecting a analogous signal of a physiological value; a conversion unit 42, connected to the detection unit 41, for converting the analogous signal to a digital signal of the physiological value; and a connection unit 43, electrically connected to the conversion unit 42 and the external electronic device 20. The external electronic device 20 computes the digital signal and obtains a heart frequency spectrum and then stores the physiological value and the heart frequency spectrum to the database 30. On the other hand, the external electronic device 20 further provides power to the electronic vital-sign monitoring device 40. In one embodiment, the connection unit 43 is a USB port or a RS232 port.

Continue the above description, the external electronic device 20 also comprises a display unit 24 for displaying information of physiological values and heart frequency spectrum. In one embodiment, the display unit 24 is LCD or LED. The external electronic device 20 can be a desktop computer, a laptop or a PDA. Users can use the external electronic device 20 to give commands to the electronic vital-sign monitoring device 40 for detection. The external device 20 can transfer the physiological value or the heart frequency spectrum to the database 30 by wired or wireless means such as wired internet, wireless internet, landline phone or mobile phone. After receiving the information of the physiological value or the diagram of the heart frequency spectrum, the database will then integrate and archive the data to enable subjects, their family members or nursing staff to view the results on the internet. Once the physiological value or heart frequency spectrum appears abnormal or exceeds threshold value, reporting mechanism will be activated to inform the subjects, their family members or nursing staff by wired or wireless means such as wired internet, wireless internet, landline phone or mobile phone.

According to the aforementioned description, the present invention incorporates a new function of detecting heart frequency spectrum into general electronic vital-sign monitoring system so that it can immediately offer information of heart status to patients, elders or general users who need regular care or instant assistance. Furthermore, the database enables subjects, their family members or general users to track information of physiological values or heart frequency spectrum by wire or wireless means such as on the internet. Via the reporting mechanism, subjects, their family members or nursing staff can be urgently informed once the physiological value or heart frequency spectrum appears abnormal or exceeds threshold value so as to achieve telecare service.

The present invention provides an electronic vital-sign monitoring system for detecting blood pressure, blood oxygen or electrocardiogram information with the novel function of detecting heart frequency spectrum. Regarding to patients, elders or general users who need regular care or instant assistance, this system can accurately determine heart status and offer necessary information of physiological values or heart frequency spectrum to family members, telecare center, hospital or nursing staff. Moreover, when using monitoring system to regularly monitor blood pressure, blood oxygen or electrocardiogram of patients, if heart frequency spectrum appears abnormal, nursing staff or related people can inquire patients about their body status. If feeling sick, further examination of the heart can be arranged in major hospitals.

In conclusion, the present invention provides an electronic vital-sign monitoring system which not only has original detection functions but also can detect heart frequency spectrum and offer telecare service. For patients, elders and general users, it can provide proper assistance according to different requirements.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. An electronic vital-sign monitoring system comprising:
   a database;
   a detection unit, for detecting a physiological value comprising blood pressure information;
   a processing unit connected to the detection unit, for computing the blood pressure information to obtain a heart frequency spectrum; and
   a transfer unit electrically connected to the processing unit, for transferring the physiological value and the heart frequency spectrum to the database.

2. The electronic vital-sign monitoring system according to claim 1, further comprising a display unit connected to the processing unit, for displaying the physiological value and the heart frequency spectrum.

3. The electronic vital-sign monitoring system according to claim 1, further comprising a memory unit connected to the processing unit, for storing the physiological value and the heart frequency spectrum.

4. The electronic vital-sign monitoring system according to claim 1, further comprising a power unit connected to the processing unit and the detection unit, for providing power.

5. The electronic vital-sign monitoring system according to claim 1, wherein the database is a cloud database or a local database.

6. The electronic vital-sign monitoring system according to claim 1, wherein the system is a single-functional system for detecting physiological values or a multifunctional patient monitoring system.

7. An electronic vital-sign monitoring device, which is connected to an external electronic device to compose an electronic vital-sign monitoring system further comprising a database, wherein the electronic vital-sign monitoring device comprises:
- a detection unit, for detecting an analogous signal of a physiological value comprising blood pressure information;
- a conversion unit connected to the detection unit, for converting the analogous signal to a digital signal of the physiological value; and
- a connection unit electrically connected to the conversion unit and the external electronic device, wherein the external electronic device computes the digital signal of the blood pressure information to obtain a heart frequency spectrum.

8. The electronic vital-sign monitoring device according to claim 7, wherein the external electronic device stores the physiological value and the heart frequency spectrum into the database.

9. The electronic vital-sign monitoring device according to claim 7, wherein the database is a cloud database or a local database.

10. The electronic vital-sign monitoring device according to claim 7, wherein the external electronic device comprises a display unit, for displaying the physiological value and the heart frequency spectrum.

11. The electronic vital-sign monitoring device according to claim 7, wherein the external electronic device provides power to the electronic vital-sign monitoring device via the connection unit.

* * * * *